(12) United States Patent
Scheler et al.

(10) Patent No.: US 9,566,337 B2
(45) Date of Patent: Feb. 14, 2017

(54) POWDER MIXTURES FOR ANTIBIOTIC DRY SYRUP FORMULATIONS

(71) Applicant: Sandoz AG, Basel (CH)

(72) Inventors: Stefan Scheler, Kundl (AT); Johannes Raneburger, Kundl (AT); Franz Xaver Schwarz, Kundl (AT); Florian Kern, Kundl (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/901,950

(22) PCT Filed: Jul. 8, 2014

(86) PCT No.: PCT/EP2014/064594
§ 371 (c)(1),
(2) Date: Dec. 29, 2015

(87) PCT Pub. No.: WO2015/007571
PCT Pub. Date: Jan. 22, 2015

(65) Prior Publication Data
US 2016/0151501 A1  Jun. 2, 2016

(30) Foreign Application Priority Data
Jul. 18, 2013 (EP) .................................... 13177076

(51) Int. Cl.
| | | |
|---|---|---|
| *A61K 47/00* | (2006.01) | |
| *A61K 47/36* | (2006.01) | |
| *A61K 9/00* | (2006.01) | |
| *A61K 31/546* | (2006.01) | |
| *A61K 31/43* | (2006.01) | |
| *A61K 31/545* | (2006.01) | |
| *A61K 47/02* | (2006.01) | |
| *A61K 47/12* | (2006.01) | |
| *A61K 47/14* | (2006.01) | |

(52) U.S. Cl.
CPC ............ *A61K 47/36* (2013.01); *A61K 9/0095* (2013.01); *A61K 31/43* (2013.01); *A61K 31/545* (2013.01); *A61K 31/546* (2013.01); *A61K 47/02* (2013.01); *A61K 47/12* (2013.01); *A61K 47/14* (2013.01)

(58) Field of Classification Search
None
See application file for complete search history.

(56) References Cited

U.S. PATENT DOCUMENTS

| 3,872,227 A | 3/1975 | Hoff | |
|---|---|---|---|
| 5,776,926 A * | 7/1998 | Bolz | ................... A61K 31/546 514/200 |

FOREIGN PATENT DOCUMENTS

| EP | 0 685 232 | 12/1995 |
|---|---|---|
| EP | 1 172 097 | 10/2000 |
| GB | 2 375 049 | 11/2002 |
| WO | 2007/017895 | 2/2007 |
| WO | 2007/119249 | 10/2007 |
| WO | 2008/089775 | 7/2008 |

OTHER PUBLICATIONS

Wagh et al. (WO2007119249A2).*
Baker et al., J. Food Sci. 1979, 45, 1370-1376.
International Search Report issued in PCT/EP2014/064594, Apr. 8, 2014, pp. 1-3.

* cited by examiner

*Primary Examiner* — Robert A Wax
*Assistant Examiner* — Quanglong Truong
(74) *Attorney, Agent, or Firm* — Jeffrey S. Melcher; Manelli Selter PLLC

(57) ABSTRACT

The present invention provides a pharmaceutical formulation prepared as dry syrups representing mere powder mixtures of beta-lactam antibiotics as active pharmaceutical ingredients and excipients without applying any other process steps than simple mixing of dry powder, whereby the pharmaceutical formulation combines two essential properties for processability and dosability: good flowability and high stability against segregation.

19 Claims, No Drawings

POWDER MIXTURES FOR ANTIBIOTIC DRY SYRUP FORMULATIONS

The invention concerns a pharmaceutical formulation prepared as dry syrups representing mere powder mixtures of active pharmaceutical ingredient (API) and excipients which combine two essential properties for processability and dosability: good flowability and high stability against segregation.

U.S. Pat. No. 3,872,227 describes a pharmaceutical composition comprising ampicillin and amino acids in tablet, granule or powder form. In order to improve the taste of the bitter ingredients a sweetening component, for example sugar, is added. As such, glucose, fructose, invert sugar, maltose, mannitol or sorbitol can be used in a concentration of 13% per weight.

U.S. Pat. No. 5,776,926 discloses pharmaceutical compositions in the form of non-aqueous suspensions which have syrup-like characteristics, characterized in that they are free of thickening substances, containing powdered sugar as a bulking agent in a preferred concentration of 25-35% by weight.

Hidekazu et al. (EP 1 172 097 B1) discloses a method for preparation of a pharmaceutical composition, which comprises suspending a hydrophobic medical compound without forming foams and excludes the conventional problems relating to the danger of explosion and the residual solvents. The method uses powdered sugar as a sweetener and flavoring agent.

It is known that both cohesion and bulk density of powdered sugar greatly affect flow properties (Baker et al., J. Food Sci. 1979, 45, 1370-1376). Particles of powdered sugars form agglomerates of many smaller individual particles that were fused into larger spherical macrostructures.

Only once the flow moisture point is reached, sugar absorbs water vapor so quickly and in such large quantities that it deliquesces and loses its flowability.

Small particles of powdered sugar have poor compression characteristics. Therefore, these small particles would have to be compressed very slowly for a long period of time to make a worthwhile tablet.

In the case of tablets, however, the use of sweeteners is limited since the amount of sugar that can be accommodated in a tablet frequently possesses inadequate sweetening power. Furthermore, the tablet composition tends to stick to the punches and dyes of the tablet-compressing machines in the case of tablets of high sugar content. Tablets containing sugar are hygroscopic and are therefore rather unsuitable for use as a vehicle for beta-lactam antibiotics.

Dry syrups are often formulations based on a huge amount of sucrose as the principal excipient.

Crystalline sucrose (refined sugar) is often used for powder mixtures because of its good flowability. However APIs and low dosed excipients with essential, concentration dependent functions, like conservants, often reveal a high de-mixing tendency particularly in process steps in which any type of gravity feeding was involved.

Dosing of large bulk quantities of powder mixtures often poses serious problems, primarily segregation of the components or bad flowability, both impeding powder filling and deteriorating content uniformity. In some cases improvements of flowability are made at the expense of segregation problems. Sometimes compaction (dry granulation) might be able to solve both problems but at the one hand it requires an additional process step causing time, efforts and costs and at the other hand there are examples for pressure sensitive APIs which do not resist the mechanical stress of a compaction process.

The present invention addresses this need and provides a wide variety of benefits and advantages. The objective therefore is to provide a formulation containing a beta-lactam antibiotic, which is characterized by an increased flowability and stability.

Thus, the present invention provides a formulation of an antibiotic dry syrup preparation prepared as a powder that combining good flowability and high segregation containing the following components:

| a beta-lactam antibiotic | |
|---|---|
| 80.0 to 95.0 wt % | powdered sugar |
| up to 1.0 wt % | a preservative |
| 0.1 to 2.0 wt % | silicon dioxide |

The advantage of the present invention is the great improvement of the segregation stability of an antibiotic powder mixture without applying any other process steps than simple mixing of dry powder. This was achieved through the use of powdered sucrose, through the amount of colloidal silicon dioxide, and by capitalizing on specific surface interactions between beta-lactam antibiotics and sucrose particles.

Experiments with a Heubach dustmeter revealed that, in contrast to other API excipient mixtures, the drug/excipient ratio in case of said beta-lactam/powdered sucrose mixtures is the same in the dust fraction as in the whole formulation, indicating a strong adhesion between the particles of a beta-lactam antibiotic and powdered sucrose. Additionally, the API improved the poor flow properties of the powdered sucrose thus enabling gravity feeding and surprisingly smooth and precise powder dosing even in commercial scale.

Beta-lactam antibiotics relate to a broad class of antibacterial agents that contains a beta-lactam ring. Preferred beta-lactam antibiotics of this invention are known or can be prepared in analogy to known processes. The more preferred beta-lactam antibiotics according to the invention are characterized by a certain degree of polarity or hydrogen bonding capability. Polar and/or hydrophilic beta-lactam antibiotics enable distinctive interaction with particles of powdered sucrose, which increases segregation stability.

Typically the formulation comprises 0.1 to 15.0 percent by weight of at least a beta-lactam antibiotic, more preferably from 1.0 to 10.0 percent by weight and most preferably from 2.0 to 8.5 percent by weight.

Beta-lactam antibiotics as antibacterial agents are effective, for example, for the following pathogens: *Citrobacter amalonaticus, Citrobacter diversus, Enterobacter* sp., *Escherichia coli, Hamophilus influenzae, Klebsiella oxytoca, Klebsiella pneumonia, Neisseria gonorrhoeae, Pasteurella multocida, Proteus mirabilis, Proteus vulgaris, Providencia* sp., *Streptococcus agalactiae, Streptococcus pneumoniae, Streptococcus pyogenes, Salmonella* sp., *Shigella* sp., *Serratia marcescens*.

Beta-lactam antibiotics are polar hydrophilic compounds, which are classified according to their ring structure and comprise penams, carbapenams, oxapenams, penems, carbapenems, monobactams, cephems, carbacephems and oxacephems. Beta-lactam antibiotics applicable in this invention are preferably characterized by a hydrocarbon scaffold containing a high amount of electronegative heteroatoms (e.g. oxygen, nitrogen, sulfur). Preferably the ratio of carbon atoms to heteroatoms is in the range from 3:1 to 1:3, more preferably from 2:1 to 1:2. The invention is in particular applicable to beta-lactam antibiotics comprising at least four polar groups substituted to the beta-lactam-ring or side chains. The polar groups of beta-lactam antibiotics are widely arranged over the whole molecule and are preferably selected form hydroxyl, carbonyl, amino, amine, amide and carboxyl.

The beta-lactam antibiotics used in the invention are active upon oral administration. Preferred beta-lactam antibiotics are selected from Cefixime, Cefpodoxime, Cefepime, Cefpirome, Ceftobiprole, Ceftazidime, Cefadroxil, Cefaclor, Cephalexin, Ceftibuten, Ertapenem, Phenoxymethylpenicillin, Flucloxacillin and Amoxicillin.

More preferably the beta-lactam antibiotic is selected from Cefixime and Amoxicillin. The most preferred beta-lactam antibiotic is Cefixime.

The term beta-lactam antibiotic includes pharmaceutical acceptable salts, hydrates and solvents as well as prodrugs of the above mentioned ingredients. The formulation might contain a mixture of beta-lactam antibiotics. The formulation might also contain an additional pharmaceutical active substance. Possible additional pharmaceutical active substances are preferably selected form inhibitors of beta lactamase (like Clavulanic acid, Sulbactam or Tazobactam). The beta-lactam antibiotic and the further active substance may be provided as separated substances or as codrug (like ampicillin and sulbactam in sultamicillin).

Despite of its known bad flowability, powdered sugar was used for preparation of beta-lactam antibiotic dry syrups instead of a crystalline sugar quality.

Experimental studies with a downpipe apparatus as well as filling tests involving gravity feeding from an upper floor to the storage tank of the filling machine one floor below did not show any segregation tendency in contrast to mixtures based on crystalline sucrose. Surprisingly the flowability of the powdered sugar formulations turned out to be much better than ever expected.

Powdered sugar according to the invention is produced by milling or grinding crystalline sugar (refined sugar crystals) to a fine powdered sugar and sieving the powdered sugar. After the conversion of crystalline bulk sugar, the average grain size of the powdered sugar is 50 µm.

Preferably at least 95% of weight, more preferred at least 97% of the powdered sugar has a particle diameter less than 250 µm, more preferred less than 210 µm.

By milling or grinding sugar crystals, sugar encapsulated water is freed, which leads to the agglomeration of many smaller individual particles of powdered sucrose into larger spherical macrostructures. It is known that both cohesion and bulk density of powdered sugar greatly affect flow properties (Baker et al., 1979).

Sugars according to the invention are hygroscopic sugars such as sucrose, dextrose, mannose and lactose which absorb significant amounts of water, e.g., greater than 5% by weight at room temperature and high relative humidity. The most preferred powdered sugar according to the invention is powdered sucrose.

When the relative humidity reaches the flow moisture point is, which for example for sugar is >80%, the sugar absorbs water vapor so quickly and in such large quantities that it deliquesces. This effect leads to a significant worse flowability.

To ensure high flowability, in one preferred embodiment of the invention, the powdered sugar is conditioned powdered sugar.

When conditioned powdered sugar is used, for example, the conditioning takes preferably place simultaneously with the milling or grinding process in conditions of absolute air humidity of at least 17 g water/kg dry air, preferably between 17 to 30 g water/kg dry air. (cf. EP 0838529 B1).

Preferably, the formulation comprises 80.0 to 95.0 percent by weight of powdered sugar, more preferably from 85.0 to 94.0 percent by weight.

The water content of a formulation according to the invention is usually determined using a method based on the Karl-Fischer titration (cf. U.S. Pat. No. 4,703,014). Preferably the formulation contains less than 4.0 percent by weight of water, preferably less than 3.0 percent by weight of water, more preferably less than 1.5 percent by weight of water, even more preferably less than 1.0 percent, most preferred less than 0.7 percent by weight of water.

The formulation of the invention comprise up to 2.0% by weight of silicon dioxide, preferably a colloidal silicon dioxide, based on the total weight of the finished formulation, more preferably from 0.5 to 1.5% by weight.

Colloidal silicon dioxide is described for example in the European Pharmacopoeia (Ph. Eur., SILICA, COLLODAL ANHYDROUS) or US Pharmacopeia (USP, Colloidal Silicon dioxide). Examples of commercial products are Aerosil (Degussa, Evonik), Dissolvurol or Entero-Teknosal.

The formulation of the present invention preferably further contains preservatives to prevent decomposition of organic matter (e.g. beta-lactam antibiotic) due to microbial contamination, when the formulation is reconstituted in water.

The preservatives are preferably selected from the group consisting sodium benzoate, sorbic acid and methyl paraben, ethyl paraben and propyl paraben, and mixtures of these compounds. A person of ordinary skill in the art will readily understand that the term "paraben" is used to refer to an alkyl ester of p-hydroxybenzoic acid.

Preferably, the concentration of the preservative employed in the present formulation ranges from 0.01 to 1.0 percent by weight, more preferably from 0.1 to 0.6 percent by weight.

Preferably, the particles of the formulation as a dry powder are characterized by a $d_{50}$ value of 40-150 µm and $d_{20}$ value less than 200 µm.

The $d_{50}$ value is called the median grain size that is the grain diameter for which half the sample (by weight) is smaller and half is larger. It is determined from the grain size distribution curve at the point where the curve crosses a horizontal line through the 50% passing value on the y axis.

The formulation of an antibiotic dry syrup preparation may comprise additional components. These include preferably a rheology modifier and a flavor agent and optionally a coloring agent.

Preferably, the claimed formulation comprises up to 1.0 percent by weight of a rheology modifier, more preferably from 0.01 to 0.6 percent by weight.

The rheology modifier preferably comprises a member selected from the group consisting of gelatinous substance selected from the group of modified polysaccharides. Modified polysaccharides are preferably carrageenans (e.g. sulfated polysaccharides), Alginic acid (e.g. anionic polysaccharides), agar (e.g. boiled polysaccharides) and Gum extract. The modified polysaccharide according to the invention is especially preferred a locust beam gum, tragacanth, guar gum, acacia gum, xanthan gum or tara gum.

The taste of a medicine can be improved by using natural or synthetic soluble flavor agents. To improve the taste of the formulation according to the invention, in certain preferred embodiments, the formulation according further comprising up to 2.0 percent by weight of a flavor ingredient based on the total weight of the finished formulation, more preferably from 0.01 to 1.5 percent by weight.

Flavor ingredients employed according to the invention are well known to those skilled in the art and are typically selected from menthol or various fruit flavors, which are based on natural, nature-identical, semi-synthetic or synthetic substances.

To provide an appealing color to an optionally taste masked formulation, coloring agents also can be incorporated in the formulation according to the invention up to 2.0 percent by weight of the finished formulation, more preferably from 0.01 to 1.5 percent by weight. Suitable coloring agents are well known to those skilled in the art and are those that are deemed safe for human consumption by relevant governmental regulatory bodies and which avoid chemical incompatibilities with other ingredients.

Preferably the formulation does not contain other components than mentioned. In particular the formulation does not contain other components that are commonly used as anticaking agents or free-flow agents, especially no starch (or derivatives thereof), no cellulose (or derivatives thereof), no talcum and no calcium salts (like calcium phosphate).

A process for producing the solid pharmaceutical formulations of the invention has also been found, wherein the sugar is added stepwise to a premix of colloidal silicon dioxide, a preservative, optionally a rheology modifier and optional additives and whereby the beta-lactam antibiotic is added to the premix with the final portion of sugar.

After mixing all compounds, the formulation is preferably dried. The drying process is more preferably done by spray-drying or evaporation.

Following up on the drying procedure, in an embodiment of the invention, the formulation is filled into bottles.

A suitable variant for the production process of the invention are as follows:

After sieving each component, a premix is prepared from a portion of the sugar (about 30%), rheology modifier, flavor, preservative, and colloidal silicon dioxide using a compulsory mixer. A beta-lactam antibiotic and the second portion of sucrose was tumble blended with the premix in a container mixer. Filling this mixture into bottles using a dry powder filling machine (e.g. auger fillers, vibration filling machine) did not reveal any segregation effects.

The formulation according to the present invention is usually used for the production of a pharmaceutical preparation, wherein the formulation is preferably is reconstituted in water before it is applied to a patient.

Before application of the formulation according to the present invention as a pharmaceutical preparation, water is added. To guarantee a homogeneous pharmaceutical preparation, the mixture shall be shaken or stirred.

The present invention is further described in the following comparative, experiments and examples, which are not intended to limit the scope of the invention.

EXAMPLE 1

Formulation 1

The following compositions are examples for successful formulations of beta-lactam antibiotic dry syrups prepared as powder mixtures combining good flowability and high segregation stability:

Powdered sucrose was produced and dried as described in U.S. Pat. No. 4,371,117.

|  | Formulation 1 | Formulation 2 | Formulation 3 |
|---|---|---|---|
| Cefixime[1] | 0.106 00 g | 0.105 g | 0.210 g |
| Powdered sucrose | 2.481 46 g[2] | 2.336 g[2] | 2.231 g[2] |
| Xanthan gum | 0.010 60 g | 0.010 g | 0.010 g |
| Strawberry flavour (FD 5930A) | 0.013 78 g | 0.013 g | 0.013 g |
| Sodium benzoate | 0.010 60 g | 0.010 g | 0.010 g |
| Colloidal silicon dioxide | 0.027 56 g | 0.026 g | 0.026 g |
| Total | 2.650 00 g | 2.500 g | 2.500 g |

[1]Drug substance is used in form of Cefixime trihydrate
[2]Varies with the initial mass of drug substance After sieving each component, a premix was prepared from a portion of the sucrose (about 30%), Xanthan gum, Strawberry flavor, Sodium benzoate, and colloidal silicon dioxide using a compulsory mixer. After elutriation, sucrose had a $d_{50}=39.2$ μm and a $d_{97}=200.9$ μm. Cefixime and the second portion of sucrose was tumble blended with the premix in a container mixer. Filling this mixture into plastic bottles using a Bausch & Ströbel dry powder filling machine did not reveal any segregation effects.

The moisture content measured according to the Karl-Fischer titration (cf. U.S. Pat. No. 4,703,014) was 0.57 percent of weight.

EXAMPLE 2

Equilibrium Moisture Content of Powder Sugar

The equilibrium moisture content of powdered sucrose was measured at two different days (12.0% (w/w), 8.3% (w/w)) and therefore an average equilibrium moisture content of 10.2% (w/w) was determined. In comparison, for a formulation based on ungrounded, crystalline sucrose RF (refined) an average equilibrium moisture content of 10.1% (w/w) (measurements at three different days: 8.9% (w/w), 9.7% (w/w), 11.6% (w/w)) was determined.

EXAMPLE 3

Segregation Experiments

To determine segregation of prepared formulations, a standardized method using a Heubach Dustmeter (Heubach GmbH, Germany) was carried out. The methodology was practiced in accordance with the German Industry Standard DIN 55 992.

For the quantification of dust, each preparation was moved in a rotary tube and simultaneously overflowed with a defined air flow. Air borne dust particles were collected onto a filter. After having determined the dust quantity by weighing the filter, the extracted dust was chemically analyzed. The left-hand side of the table below shows the respective quantity of air borne dust particles in relation to the total powder quantity, which were collected by the filter. Segregation experiments of type I and type II vary in their experimental arrangement. In type II experiments an additional separator is positioned in front of the filter allowing only very small air borne particles to arrive at the filter. The right hand-side of the table exhibits the filter deposited relative dust fraction for both critical components of the powder mixture (active ingredient and preservative), measured as a percentage enrichment of each component in relation to the initial concentration of the tested powder mixture. The commercial available product Suprax® is a Cefixime-based powder mixture containing crystalline sucrose. The selective removal of the active ingredient in the air flow suggests low adhesion forces between the active ingredient and sucrose crystals. The product Suprax® used as a comparative example is a granulate.

The manufacturing process explains the strong interaction between Cefixime and sugar in the invention, which leads its high segregation stability. The pure, ungranulated mixture of Cefixime and powdered sucrose according to the invention has the highest segregation stability. The Cefixime-specific adhesion on powdered sucrose is also apparent in comparison to sodium benzoate as preservative.

|  |  | Dust content [%] | Enrichment [%] | |
|---|---|---|---|---|
|  | Experiment |  | Active incredient | Sodium benzoate |
| Suprax ® (comparative example) | Type I | 3.0 | 510 | 238 |
|  | Type II | 0.5 | 613 | 210 |
| Ratiopharm standard sugar mixture (comparative example) | Type I | 1.9 | 26 | 248 |
|  | Type II | 0.5 | 30 | 130 |
| Cefixime/powdered sucrose | Type I | 4.2 | 6 | 206 |
|  | Type II | 0.6 | 8 | 178 |

EXAMPLE 4

Influence of Colloidal Silicon

The influence of colloidal silicon (e.g. Aerosil) as flowability-regulating agent was determined using a Freeman powder rheometer, which records the energy input, when agitating powder mixtures with different stirring speeds. Therefore, three different formulations with equal Cefixime concentrations of 100 mg/5 ml and different concentrations of the Aerosil 1.0%, 0.5%, 1.5%) were compared. The basic flowability energy (BFE) was determined as 345 mJ, 440 mJ, and 620 mJ for 1.5%, 0.5%, and 1.0% Aerosil, respectively. This demonstrates that the flowability decreases with decreasing amount of Aerosil from 1.5 to 1.0%, but increases again, when reducing the Aerosil amount to 0.5%.

The invention claimed is:

1. Formulation of an antibiotic dry syrup preparation prepared as a powder that combining good flowability and high segregation stability containing the following components:
   a beta-lactam antibiotic;
   80.0 to 95.0 wt % powdered sugar;
   up to 1.0 wt % a preservative; and
   up to 2.0 wt % silicon dioxide.

2. The formulation according to claim 1 as a dry powder with a maximum water content of 3 percent by weight.

3. The formulation according to claim 1, wherein the particles of the powder having a $d_{50}$ value of 50-150 μm and a $d_{90}$ value less than 200 μm.

4. The formulation according to claim 1, wherein a beta-lactam antibiotic is present in a concentration from 0.1 to 15.0 percent by weight.

5. The formulation according to claim 1, wherein the beta-lactam antibiotic is selected from Cefixime and Amoxicillin.

6. The formulation according to claim 1, containing an additional pharmaceutical active substance.

7. The formulation according to claim 1, wherein at least 97 wt % of the powdered sugar has a particle diameter less than 210 μm.

8. The formulation according to claim 1, wherein the powdered sugar is conditioned powdered sugar.

9. The formulation according to claim 1, wherein the said powdered sugar is powdered sucrose.

10. The formulation according to claim 1, wherein the preservative is selected from sodium benzoate, sorbic acid and parabens.

11. The formulation according to claim 1, further comprising up to 1.0 percent by weight of a rheology modifier.

12. The formulation according to claim 1, further comprising 0.01 to 2.0 percent by weight of a flavor ingredient.

13. Process for manufacturing a formulation according to claim 1, comprising adding the powdered sugar stepwise to a premix of colloidal silicon dioxide, a preservative, optionally a rheology modifier and optional additives and subsequently adding the beta-lactam antibiotic to form the formulation.

14. The process according to claim 13, further comprising drying the formulation to less than 4.0 percent by weight of water.

15. The process according to claim 14, wherein the formulation is spray-dried or dried by evaporation.

16. The formulation according to claim 1, wherein the formulation is a pharmaceutical preparation.

17. A method of treating a patient, comprising reconstituting the formulation according to claim 16 in water and having the patient drink the reconstituted formulation.

18. The formulation according to claim 11, wherein the rheology modifier is selected from the group of modified polysaccharides.

19. A powdered formulation of an antibiotic dry syrup preparation combining good flowability and high segregation stability comprising:
   a pharmaceutically effective amount of a beta-lactam antibiotic;
   80.0 to 95.0 wt % powdered sugar;
   up to 1.0 wt % preservative; and
   up to 2.0 wt % silicon dioxide, wherein the formulation is in the form of a dry powder having a maximum water content of 3 percent by weight, and particles of the dry powder having a $d_{50}$ value of 50-150 μm and a $d_{90}$ value less than 200 μm.

* * * * *